United States Patent

Izraelev

[11] Patent Number: 5,924,848
[45] Date of Patent: Jul. 20, 1999

[54] BLOOD PUMP HAVING RADIAL VANES WITH ENCLOSED MAGNETIC DRIVE COMPONENTS

[75] Inventor: Valentin M. Izraelev, Eden Prairie, Minn.

[73] Assignee: Advanced Bionics, Inc., Eden Prairie, Minn.

[21] Appl. No.: 08/886,385

[22] Filed: Jul. 1, 1997

Related U.S. Application Data

[63] Continuation-in-part of application No. 08/456,503, Jun. 1, 1995, Pat. No. 5,685,700.

[51] Int. Cl.$^6$ .................................................. F04B 17/00
[52] U.S. Cl. .................... 417/420; 417/356; 417/423.14; 415/900; 416/186 R
[58] Field of Search .................................. 415/203, 206, 415/900; 600/16; 604/4, 131, 151; 417/420, 423.14, 423.7, 424.1, 356, 357; 623/3; 416/186 R, 189

[56] References Cited

U.S. PATENT DOCUMENTS

| | | |
|---|---|---|
| 2,319,730 | 5/1943 | Garraway . |
| 3,433,163 | 3/1969 | Sheets et al. . |
| 3,647,324 | 3/1972 | Rafferty et al. ......................... 417/420 |
| 3,890,019 | 6/1975 | Boden et al. . |
| 3,957,389 | 5/1976 | Rafferty et al. . |
| 3,970,408 | 7/1976 | Rafferty et al. . |
| 4,036,565 | 7/1977 | Becker . |
| 4,057,369 | 11/1977 | Isenberg et al. . |
| 4,507,048 | 3/1985 | Belenger et al. ......................... 417/90 |
| 4,688,998 | 8/1987 | Olsen et al. . |
| 4,779,614 | 10/1988 | Moise . |
| 4,944,748 | 7/1990 | Bramm et al. . |
| 4,994,078 | 2/1991 | Jarvik . |
| 4,995,857 | 2/1991 | Arnold . |
| 5,049,134 | 9/1991 | Golding et al. . |
| 5,055,005 | 10/1991 | Kletschka . |
| 5,078,741 | 1/1992 | Bramm et al. . |
| 5,112,200 | 5/1992 | Isaacson et al. . |
| 5,158,440 | 10/1992 | Cooper et al. . |
| 5,195,877 | 3/1993 | Kletschka . |
| 5,205,721 | 4/1993 | Isaacson . |
| 5,211,546 | 5/1993 | Isaacson et al. . |
| 5,326,344 | 7/1994 | Bramm et al. . |
| 5,385,581 | 1/1995 | Bramm et al. . |
| 5,443,503 | 8/1995 | Yamane . |
| 5,470,208 | 11/1995 | Kletschka . |

FOREIGN PATENT DOCUMENTS

| | | |
|---|---|---|
| 2342767 | 3/1975 | Germany . |
| 3130974 A1 | 2/1983 | Germany . |
| 1359007 | 7/1974 | United Kingdom . |

OTHER PUBLICATIONS

Olsen et al., "Blood Pump with a Magnetically Suspended Impeller", *Trans. Am. Soc. Artif. Intern. Organs*, vol. XXXI, 1985, pp. 395–401.

(List continued on next page.)

*Primary Examiner*—Charles Freay
*Attorney, Agent, or Firm*—Haugen Law Firm PLLP

[57] ABSTRACT

A pump for transferring fragile and aggressive fluids such as human blood and comprising a pumping chamber along with a pair of fluid inlet ports arranged in oppositely disposed relationship on the chamber, and one or more outlet ports arranged transversely and medially of the inlet ports. A rotor is positioned within the pumping chamber having a dual-conical configuration converging toward opposed polar end regions and with an axis of rotation extending between the polar regions. The rotor includes a plurality of radial vanes mounted on the outer surface of the dual cones forming the dual-conical configuration, and with the radially outward tips of the vanes encapsulating permanent magnets, with the vanes and permanent magnets being arranged at equally radially spaced locations. A magnetic drive is positioned to deliver rotational driving energy to the magnets in the rotor. The sole support for the rotor are the hydrodynamic forces acting upon the rotor during its operation, with the rotor body having a relative density of between 10% and 90% of the relative density of the fluid being pumped.

9 Claims, 3 Drawing Sheets

OTHER PUBLICATIONS

Bramm et al., "The Sealless and Bearingless Rotor Blood Pump System: Adaptation . . . Thermal Heat Up" Assisted Circulation 3, F. Unger (Ed.), Springer–Verlag Berlin Heidelberg, 1989, pp. 215–224.

Ohara et al., "The Next Generation Baylor C–Gyro Pump: Anthithrombogenic 'Free Impeller' Design for Long–Term Centrifugal VAD", *Artif. Organs*, vol. 18, #3, 1994, pp. 238–243.

Treichler et al., "A Fluid Dynamic Analysis of a Rotary Blood Pump for Design Improvement", *Artif. Ogans*, vol. 17, No. 9, pp. 797–808.

Nishida et al., "Development of the Terumo Capiox Centrifugal Pump and Its Clinical . . . Roller Pump", *Artif. Organs*, vol. 17, No. 4, 1993, pp. 323–327.

Araki et al., "A Flow Visualization Study of Centrifugal Blood Pumps Developed for Long–Term Usage", *Artif. Organs*, vol. 17, No. 5, 1993, pp. 307–312.

Bramm et al., "Reduction of Coagulation and Hemolysis . . .for Long–Term Application", pp. 175–179.

Sasaki et al., "A Compact Centrifugal Pump for Cardiopulmonary Bypass", *Artif. Organs*, vol. 16, No. 6, 1992, pp. 592–598.

Ohara et al., "An Ultimate Compact, Seal–less Centrifugal Ventrigular Assist Device: Baylor C–Gyro Pump", *Artif. Organs*, vol. 18, No. 1, 1994, pp. 17–24.

Makinouchi et al, "Internal Hydraulic Loss in a Seal–less Centrifugal Gyro Pump",*Artif. Organs*, vol. 18, No. 1, 1994, pp. 25–31.

Kijima, et al, "The Margin of Safety in the Use of a Straight Path Centrifugal Blood Pump", *Artif. Organs*, vol. 18, No. 9, 1994, pp. 680–686.

Araki et al, "A Flow Visualization Study of the NCVC Centrifugal Blood Pump", *Artif. Organs*, vol. 18, No. 9, 1994, pp. 669–672.

Kabei et al, "Concept Designs of Nonrotating–type Centrifugal Blood Pump . . . Disc–type Centrifugal Pump",*Artif. Organs*, vol. 18, No. 9, 1994, pp. 657–663.

Schima et al., "The Vienna Implantable Centrifugal Blood Pump", *Artif. Organs*, vol. 18, #7, 1994, pp. 500–505.

Ohara et al., "Development and Evaluation of Antithrombogenic Centrifugal Pump: The Baylo . . . Inlet Port Model", *Artif. Organs*, vol. 18, No. 9, 1994, pp. 673–679.

Taguchi, et al., "A Miniaturized Centrifugal Pump for Assist Circulation", *Artif. Organs*, vol. 18, No. 9, 1994, pp. 664–668.

Akamatsu et al., "Centrifugal Blood Pump with a Magnetically Suspended Impeller", *Artif. Organs*, vol. 16, No. 3, 1993, pp. 305–308.

Miller et al., "Evaluation of Multiple Disk Centrifugal Pump as an Artificial Ventricle", *Artif. Organs*, vol. 17, No. 7, 1993, pp. 590–592.

Ohara et al., "Baylor Gyro Pump: A Completely Seal–less . . . Long–Term Circulatory Support", *Artif. Organs*, vol. 17, No. 7, 1993, pp. 599–604.

Schima et al., "In Vitro Investigation of Thromboenesis in Rotary Blood Pumps", *Artif. Organs*, vol. 17, No. 7, 1993, pp. 605–608.

Kijima et al., "A Straight Path Centrifugal Blood Pump Concept in the Capiox Centrifugal Pump", *Artif. Organs*, vol. 17, No. 7, 1993, pp. 593–598.

Naito et al., "Developments of the Baylor–Nikkiso Centrifugal Pump with . . . Circulatory Support", *Artif. Organs*, vol. 17, No. 7, 1993, pp. 614–618.

Damm et al., "In Vitro Performance of the Baylor/NASA Axial Flow Pump", *Artif. Organs*, vol. 17, #7, 1993, pp. 609–613.

Yada et al., "Clinical Experience Using the Bio–Pump for Extracorporeal Circulation during Open–Heart Surgery", *Artif. Organs*, vol. 17, No. 7, 1993, pp. 619–624.

Nishida et al., "Clinical Experience of Assisted Circulation with . . . Women's Medical College",*Artif. Organs*, vol. 17, No. 7, 1993, pp. 625–629.

Curtis et al., "Clinical Experience with the Sarns Centrifugal Pump", *Artif. Organs*, vol. 17, No. 7, 1993 pp. 630–633.

Affeld et al., "A New Electrohydraulic Energy Concerter for a Left Ventricular Assist Device",*Artif. Organs*, vol. 18, No. 7, 1994, pp. 479–483.

Curtis et al., "Frequency of Seal Disruption with the Sarns Centrifugal Pump in Postcardiotomy Circulatory Assist", *Artif. Organs*, vol. 18, No. 3, 1994, pp. 235–237.

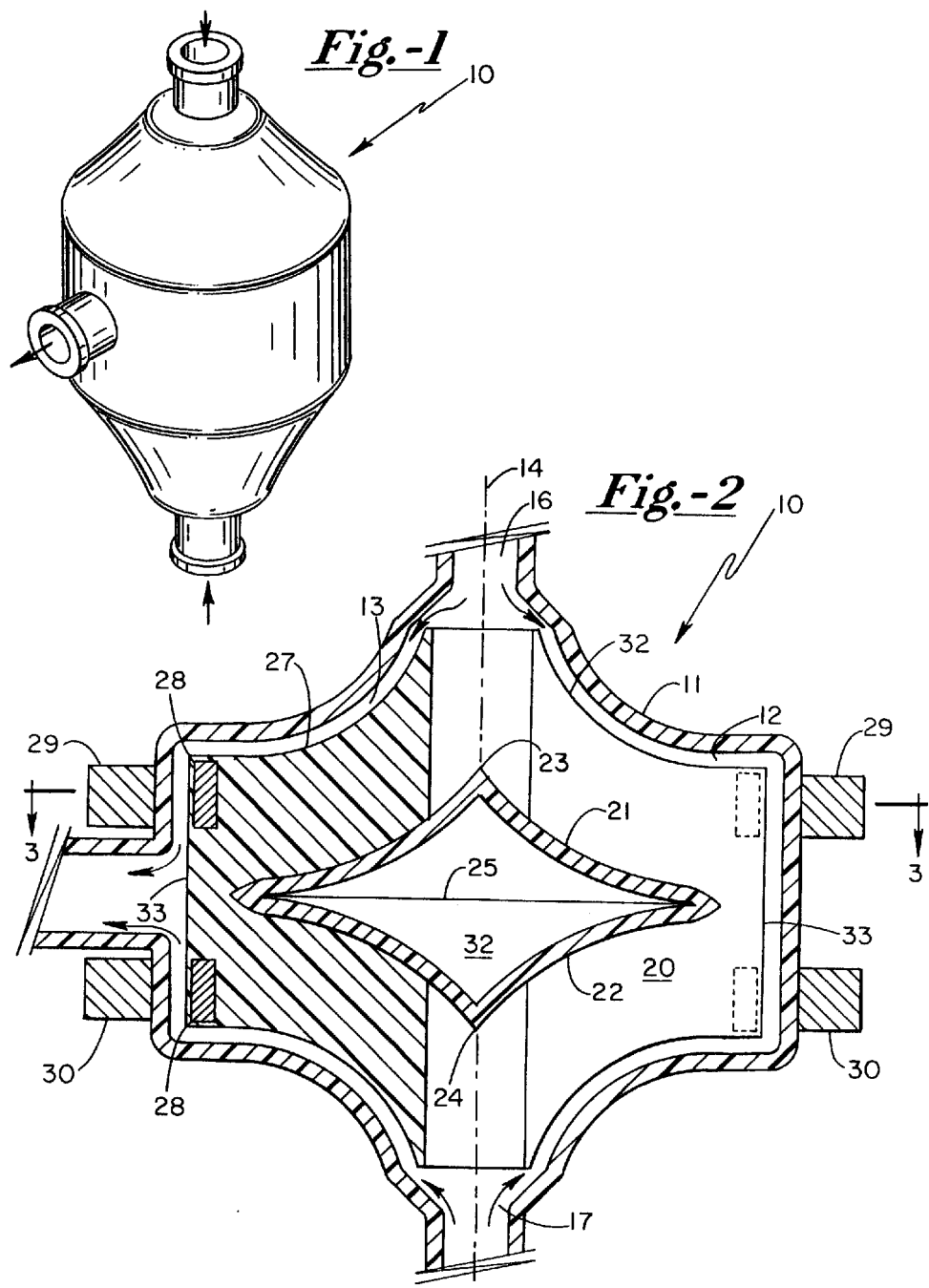

BLOOD PUMP HAVING RADIAL VANES WITH ENCLOSED MAGNETIC DRIVE COMPONENTS

CROSS-REFERENCE TO RELATED APPLICATION

The present application is a continuation-in-part of my application Ser. No. 08/456,503, filed Jun. 1, 1995, entitled "BLOOD PUMP", now U.S. Pat. No. 5,685,700, issued Nov. 11, 1997 and assigned to the same assignee as the present invention.

BACKGROUND OF THE INVENTION

The present invention relates generally to an improved pump having a rotor with radial vanes thereon, and wherein the vanes enclose and/or encapsulate magnetic drive components. The pump of the present invention is particularly useful in transferring fragile and/or aggressive fluids. Examples of fragile fluids include human or animal blood, neither of which can tolerate exposure to unusual impact and/or sheer forces. Aggressive fluids include corrosive or poisonous fluids, as well as fluids which cannot tolerate contamination, or which otherwise may destroy seals and/or bearings to reduce the lifetime and/or longevity of the pump structure. Poisonous fluids, for example, are extremely dangerous if a leak develops. More particularly, the present invention relates to a pump which is bearing and seal-free and wherein during operation, the rotor is dynamically balanced by a combination of hydrodynamic and buoyant forces. The pump of the present invention is particularly adapted for transferring human blood and is capable of creating a flow of such liquids without damaging and/or otherwise adversely affecting the quality of the material being pumped. The rotor employed in the pump of the present invention is rotated electromagnetically by means of an electromagnetic drive system operating in conjunction with an array of permanent magnets enclosed within radial vanes on the surface of the rotor, the drive components being arranged in a brushless motor configuration. Alternatively, a permanent magnet-to-permanent magnet coupling may be employed. As such, the arrangement of the present invention provides a symmetrical arrangement which is capable of achieving relative rotation while at the same time being bearing and seal-free.

In the past, pumps and pumping systems have been designed which have been characterized as being bearing and seal-free. Such systems typically employ magnetic levitation means which is in effect an actual form of bearing, much the same as sleeve bearings, ball bearings, or other friction-inducing bearings. Such arrangements using magnetic bearings, while being operational and functional, may be rendered complex and accordingly require significant number of additional components including magnetic devices, position sensors, and rapid-response magnetic drive means. A number of such patents have been granted in the past, including those to Olsen et al. U.S. Pat. Nos. 4,688,998 and 5,195,877. The apparatus of the present invention, by contrast, is fully bearing and seal-free, with dynamic balance being achieved through a combination of hydrodynamic and buoyant forces. In this connection, the rotor of the pump of the present invention is provided with a symmetrical arrangement of radial vanes which enclose components of the magnetic drive so as to enhance and preserve the dynamic balance.

Among the disadvantages inherent in pumps utilizing friction-reducing bearings include local heat generation such as may occur from the use of ball bearings, friction bearings, sleeve bearings, and the like. Low flow and high pressure may result in local areas due to the use of such structures. In addition, with all such bearing-equipped pumps, a high spring constant is provided wherein a small displacement of the rotor (or impeller) introduces very high forces which can damage or effectively destroy bearings. In addition, different forces are introduced in the structure whenever variations in axial positions occur.

In the present structure, the pump is bearing and seal-free, with the effective low compliance of the rotor allowing for relatively high displacement without the creation of large forces otherwise required to hold the rotor in its predetermined position. In addition, the rotor seeks and finds an equilibrium position during operational rotation, which in certain situations can be off-set from the housing axis in either the rotational or transverse axes. This typically occurs when motion or movement is experienced so that the rotational axis of the pump is altered. For example, rotational movement of the pump housing will be manifested in displacement of the rotational or vertical axis of the rotor. The present arrangement has been found to eliminate the need for a highly precise axis in design, fabrication and operation. The lack of a positionally fixed rotational axis reduces the introduction of large forces which otherwise would be created when the axis of the rotor is shifted away from its normal centrally disposed position.

In the arrangement of the present invention, the pump includes a pumping chamber with a central axis, and with a rotor body being disposed within the chamber for bearing and seal-free rotation therewithin. The rotor has a double or dual-conical configuration which converges toward opposed polar regions, and with the axis of rotation extending between these polar regions. The rotor is further provided with radial vanes extending radially outwardly relative to the axis of rotation. These vanes are utilized to enhance flow, as well as to provide a zone for encapsulation of magnetic drive components. Magnetic drive components are typically arranged symmetrically in axially spaced-apart relationship relative to the transverse axis of the rotor. Fluid inlet ports are arranged in the pumping chamber in oppositely disposed relationship within the chamber, with the fluid being transported or transferred to the inlet port area either externally or internally of the chamber. Except for those occasions when the rotor is displaced, it is normally arranged in coaxial relationship with both the pumping chamber and the fluid inlet ports. The outlet port or ports are arranged generally medially of the chamber, midway between the inlet ports and typically are positioned tangentially of the medial portion of the pumping chamber. In those situations where the axis of rotation of the rotor is arranged along a vertical axis, the dual-conical configuration is such that flow on the outside portion of the rotor proceeds downwardly on the upper portion, and upwardly on the lower portion of the dual-cone rotor.

An example of an external transfer of fluids between the oppositely disposed fluid inlet ports is a fluid transfer line which introduces the fluids at opposite ends of the housing. As an example of an internal transfer, a bore may be provided which extends between opposite ends of the rotor, thereby permitting transfer of fluids internally of the structure.

The term "oppositely disposed inlet ports" is intended to reflect the utilization of fluid introduction at opposite ends of the rotor, and is also intended to include those arrangements wherein all of the fluid being pumped is initially introduced into one polar region of the housing, with the fluid nevertheless being transferred either internally or externally of the housing directly to the oppositely disposed polar region.

The pump shown in the drawings is in operational mode with the rotor spinning about its axis of rotation and with all forces acting on the rotor balanced. In the stationary/non-operational mode with the fluid in the housing, only the buoyant forces are acting on the rotor, and the rotor floats up in the random position. In the stationary/non-operational mode with no fluid in the housing, the rotor is resting on the interior of the housing under gravitational forces.

Levitation of the rotor, as indicated, is achieved by a combination of hydrodynamic and buoyant forces. Briefly, the buoyant component is achieved as a result of careful selection of the rotor density, with the preferred relative density being between about 0.1 and 0.9 of the relative density of the fluid being pumped. In a dynamic and operational mode, the buoyant forces merely become a component of lesser or secondary importance to the more significant and more highly effective hydrodynamic force.

The hydrodynamic force component is achieved as a result of the motion of the fluid as it is being moved through the pumping chamber. As the velocity of the fluid increases, the hydrodynamic forces increase substantially, and with the proper selection of rotor density, the hydrodynamic forces which are created during normal operation result in achieving a precise, steady and controllably repeatable centering of the rotor within the pumping chamber.

The pump structure of the present invention has particular application for transferring fragile and/or aggressive liquids, in particular, for transferring human blood. Since certain components in blood are extremely fragile and are damaged upon exposure to external forces, conventional pumps are simply unsuited for the application. Additionally, conventional seals and/or bearings typically found within conventional pump structures pose substantial and significant threats to cell damage. A further feature of the pump of the present invention rendering the pump well suited for transfer of blood is its essentially friction-free operation. Any frictional force creates the risk of generation of thermal energy, and thus may contribute to heat build-up. Since blood is extremely sensitive to temperature change, particularly any increase in temperature above conventional body temperature, reduction and/or virtual elimination of friction provides significant and substantial advantages.

Since the structure of the present invention does not require bearings, energy consumption is reduced through the elimination of energy losses otherwise occurring in the bearings, including energy lost in contact bearings as well as electrical losses in magnetic bearings. The driving forces for the impeller are located generally in planes closely spaced from and symmetrical to the center of gravity or center of mass of the impeller. This feature results in the creation of a gyroscopic effect of a free-body gyroscope, and the configuration of the present invention is such as to stabilize the impeller when the axis of the housing is rotated relative to the spin axis of the rotor. In other words, the spin axis of the rotor may be altered because of a change-of-position of the housing, and thus the spin axis may not always be about the vertical axis, but can be about the horizontal axis as well. The elimination of shafts, bearings and seals substantially reduces the manufacturing cost of the present pump. Also, the present pump has a virtual unlimited mechanical life under normal conditions. The device of the present invention finds utility for any fluids when economy, longevity, and uninterrupted service are the factors.

In addition to blood pump applications, the device of the present invention finds utility in connection with other fluids as well. Certainly non-delicate fluids may be appropriately treated and/or moved with pump devices of the present invention including the aggressive fluids as discussed hereinabove.

One object of the present invention is to bring the fluid from the opposite inlet regions of the housing to the medial plane of the housing, combine in the medial plane two opposite flows, and deliver the fluid to the outlet port or ports with minimal damage and losses to the fluid being pumped through avoidance of turbulence, flow separation, sharp turns, stagnation, and other undesired conditions. This is achieved by combining the upper and lower pair of respective vanes in the single unit at the outlet region, encapsulating the permanent magnets into the vanes at the outer tips of the vanes, and by moving the electromagnetic drive means from the median plane of the housing and the rotor.

SUMMARY OF THE INVENTION

Therefore, it is a primary object of the present invention to provide an improved pump for transferring fragile liquids such as human blood, and wherein the pump is bearing and seal-free, with the rotor having radial vanes enclosing magnetic drive components adjacent the radial outer ends thereof, and with the rotor being dynamically balanced by a combination of hydrodynamic and buoyant forces.

It is yet a further object of the present invention to provide an improved pump for application with human blood which is capable of creating a uniform and consistent flow of such liquids without damaging or otherwise adversely affecting the quality of the material being pumped.

It is yet a further object of the present invention to provide a pump structure utilizing a pumping chamber housing a rotor wherein rotation of the rotor is achieved by an electromagnetic drive system operating in conjunction with an array of permanent magnets distally positioned in radial vanes mounted on the rotor and arranged in a brushless configuration.

Other and further objects of the present invention will become apparent to those skilled in the art upon a study of the following specification, appended claims, and accompanying drawings.

IN THE DRAWINGS

FIG. 1 is a perspective view of a pump assembly prepared in accordance with the present invention;

FIG. 2 is a vertical sectional view of the assembly and taken through the axis of rotation of the rotor portion of the structure as illustrated in FIG. 1, with FIG. 2 being taken along the line and in the direction of the arrows 2—2 of FIG. 3, and further illustrating the arrangement of the drive components of the pump;

DESCRIPTION OF THE PREFERRED EMBODIMENT

Figure 3:
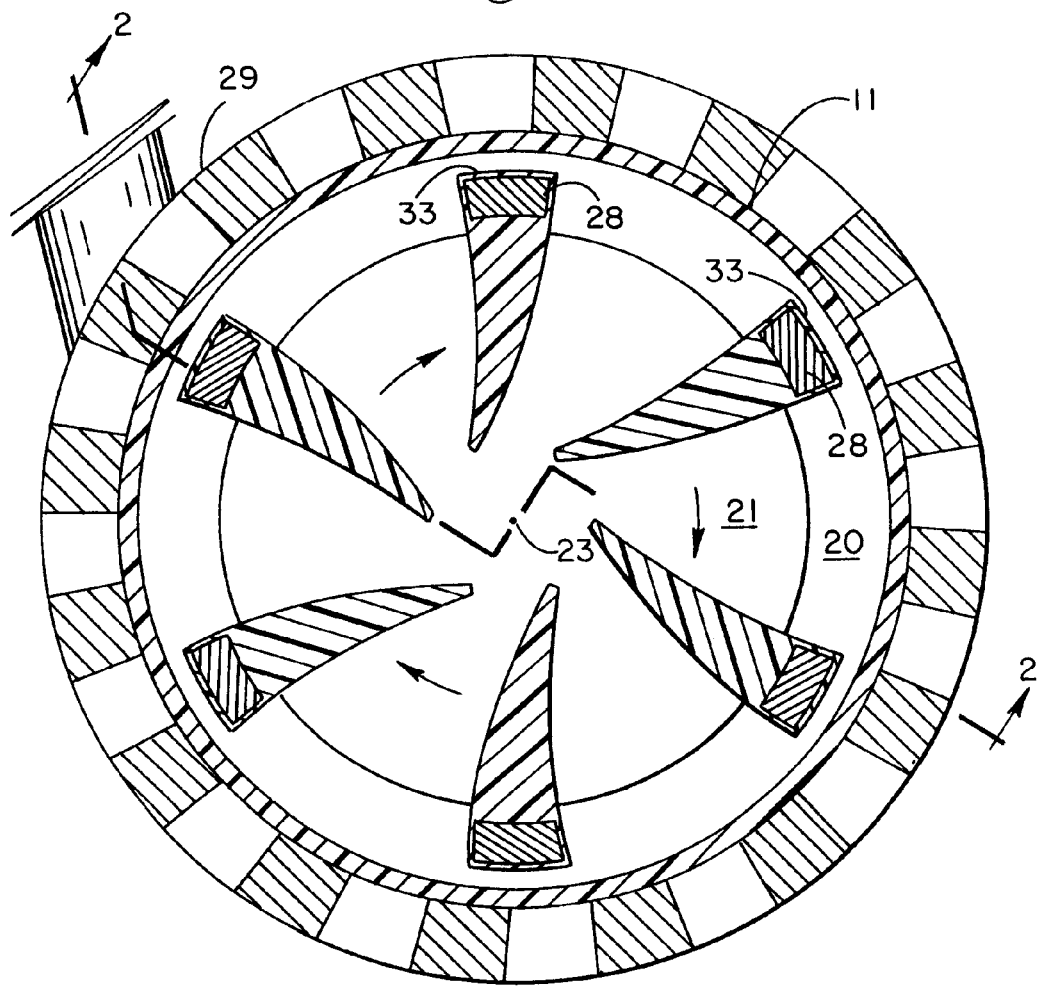
FIG. 3 is a horizontal sectional view of the pump taken along the line and in the direction of the arrows 3—3 of FIG. 2.

In accordance with the preferred embodiment of the present invention, and with particular attention being directed to FIGS. 1, 2 and 3 of the drawings, the pump generally designated 10 comprises a housing 11, the interior of which defines pumping chamber 12. In other words, the inner periphery 13 of housing 11 is the outer periphery of the chamber 12. As is clear from the views of FIGS. 2 and 3, housing 11 and chamber 12 share a central axis which extends along axis 14 as set forth in FIG. 2. Housing 11, and accordingly chamber 12, is provided with a pair of inlet ports as at 16 and 17, along with an outlet port as at 18. Inlet ports 16 and 17, collectively, define the inlets to the chamber, while outlet port 18 define the outlet. The inlet ports 16 and 17 are arranged coaxially with the chamber, that is, along axis 14, with the inlet ports being arranged in oppositely disposed relationship to chamber 12. Outlet port 18 is arranged medially of the inlet ports, and is, as indicated, disposed generally transversely of axis 14. It should be noted that multiple outlet ports may be utilized, and in such an event, each port is typically arranged medially of the inlet ports, consistent with the arrangement illustrated for outlet port 18.

With continued attention being directed to FIGS. 2 and 3 of the drawings, rotor generally designated 20 is disposed within chamber 12 and has a modified symmetrical dual conical configuration. This configuration provides dual cones 21 and 22 converging toward opposed polar regions such as 23 and 24, and the rotor is provided with an axis of rotation which extends between the polar regions 23 and 24, which is normally consistent with and coaxially with axis 14. The base of each of the two cones forming the dual cone configuration are coupled together and form a common center plane 25. The outer surfaces of dual cones 21 and 22 are provided with a plurality of radial vanes such as at 27—27. Vanes 27—27 are arranged with surface portions extending axially and radially of the outer surfaces of cone members 21 and 22, as is illustrated and shown in FIG. 2. In addition, vanes 27—27 are utilized as a mounting base for a plurality of permanent magnets such as magnets 28—28. These magnets are arranged at radially spaced locations generally equally axially spaced from center plane 25 and radially outwardly of the axis of rotation of rotor 20. The permanent magnets 28—28 are provided at equally radially and arcuately spaced locations. Electromagnetic drive means are provided as at 29—29 and 30—30, with the electromagnetic drive means being, in turn, coupled to a source of electrical energy and arranged to deliver rotational driving energy to the rotor through the permanent magnets 28—28. The drive arrangement is, of course, commonly referred to as a brushless motor configuration and brushless motor drives are, of course, well known in the art. The rate of rotation of rotor 20 is conveniently controlled by means of the frequency of the field applied to electromagnetic members 29—29 and 30—30, with the rate of rotation being controlled by the frequency of the applied electromagnetic field, or by selective energization of the electromagnetic means 29—29 and 30—30. Such drives are, of course, commonly utilized and well known in the art.

The material of construction of rotor 20 is either similar or identical to that employed in housing 11. A suitable biocompatible material such as polycarbonate, acrylic, or copolymers of polystyrene may be employed, or alternatively a coating may be applied to a suitable substrate in order to enhance the biocompatibility of the structure. In those instances where the device is not being employed for implantation, then, of course, other materials may be employed, provided that the blood-contacting surfaces be formed and/or coated with a non-thrombogenic material.

Figure 4:
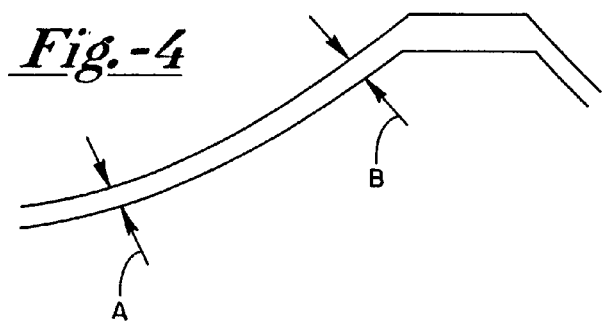
FIG. 4 is a fragmentary sectional view taken on a slightly enlarged scale and illustrating the clearance between the rotor and housing, and illustrating the manner in which a portion of the fluid flows through the assembly.

Rotor 20 is provided with a hollow core or void chamber area as shown generally at 32, with this volume or area providing a means for controlling the relative density of the rotor body. Preferably, the relative density is selected by the ratio of the relative density of the rotor to that of the fluid being pumped, and in most applications, the relative density of the rotor to the fluid being pumped is between about 0.3 and 0.6, with it being understood that relative densities of between about 0.1 and 0.9 may be found useful. Also, the dual conical configuration of rotor 20 provides the finished structure with an axial length along the axis of rotation as being generally equal to the axial length of the pumping chamber between the inlet ports 16 and 17. The transverse diameter of the rotor 20 is defined along a medial plane, as along medial line 25 and with the configuration of the dual converging cones and the radial vanes providing a clearance between the surface of the vanes of the rotor and the inner surface of the pumping chamber as illustrated in greater detail in FIG. 4. Generally speaking, the clearance as indicated at A—A and B—B is such that the clearance remains constant from the inlet port area to the outlet port area, however this clearance may be slightly divergent or slightly convergent toward the outlet. The spacing between the periphery of the vanes as at 32 and the outer surface of dual cones 21 and 22 is preferably approximately constant, and also generally parallel to the inner surface 13 of housing 11. With the volume available for transfer of the fluid being pumped, the meridional velocity of the pumped fluid remains generally constant during its passage through the pump as it moves along its translational and rotational paths and/or vectors. With these considerations in mind, the clearance between the inner surface of the pumping chamber and the outer edges of the radial vanes 27—27 or rotor 20 preferably ranges from between about 1 millimeter up to about 7 millimeters, with a narrower range of between about 1 millimeter and 3 millimeters being generally preferred. Generally, a clearance of about 1.5 millimeters is preferred, with this spacing being dimensionally illustrated at the zone between opposed arrows A—A and B—B of FIG. 4.

With respect to the areas of the inlet and outlet ports, it is generally preferred that the combined area of the inlet ports be generally equal to the combined areas of the outlet port or ports, thereby providing more consistency in flow and pressures, and also providing for an appropriate hydrodynamic balancing of the rotor 20 within the chamber 12.

The permanent magnets 28—28 are encapsulated within the radial vanes 27—27. As illustrated in FIG. 2, the physical position of the encapsulated permanent magnets 28—28 is generally closely adjacent the outer radial edge surface of vanes 27—27, with the radially outward edge surface being illustrated at 33.

As has been indicated, the drive means for the electromagnetic drive elements 29—29 and 30—30 is preferably in the form of conductor windings, and for purposes of achieving appropriate hydrodynamic balance, the windings are carefully controlled and selectively made so as to preserve the hydrodynamic balance of the rotating rotor while eliminating the need for any form of bearing.

The moment of inertia of the rotor or impeller is effectively minimized by virtue of the positioning of the mass of the impeller closer to the center of gravity or center of mass. This may be obtained by moving the mass of the impeller needed for structural integrity closer to the center, and generally as closely as possible to the rotational axis. The moment of inertia may be controllably adjusted in connection with the structure of the present invention by arranging and mounting the permanent magnets within a circular or annular zone which is at the maximum radius of the rotor inner impeller, as required, while at the same time increasing the strength of the structure along its axis of rotation.

With respect to the fluid being pumped, it should be noted that the human blood has a viscosity of about 4 centipoises at 25° C., and this viscosity is sufficient to adequately provide for sufficient friction between the vanes and rotor surface against the blood so as to achieve a sufficient rotational component of motion for hydrodynamic balancing. As the rotational velocity of the fluid being pumped increases, its hydrodynamic balance effect will, of course, increase correspondingly and proportionately. With a rotational velocity of approximately 1000 rpm, the hydrodynamic balancing effect substantially overwhelms the buoyant effect afforded by the relative density of the rotor within the chamber.

For start-up purposes, saline is normally preferred as the functional material, with the saline being employed for a period of time until the desired rotational velocity is achieved, and thereafter blood may be introduced as the working solution being pumped and/or transferred.

The inlet and outlet diameters are preferably 7 millimeters and the relative density is preferably between 0.1 to 0.9, with a relative density of 0.5 being preferred.

For most operational purposes, an inlet pressure ranging from between about 5 millimeters of Hg (mercury) up to about 40 millimeters Hg (mercury) is considered normal and appropriate for fluid dynamics dealing with human blood. Outlet pressures of between about 40 millimeters Hg (mercury) up to about 150 or 200 millimeters Hg (mercury) may be employed. When the device of the present invention is functioning as an implantable unit, the outlet pressure will, of course, depend upon the patient's activity and circulatory requirements being indicated.

The pump device of the present invention may be utilized as a patient-assist unit, with the pump being employed as a device with the outlet or outlets coupled to the aorta. In an alternative construction, the outlet may be coupled to the pulmonary artery. As indicated, the device of the present invention has application as a transfer pump as well, and may be employed, therefore, in surgical procedures which involve temporarily removing and/or temporarily disabling the heart function.

Figure 5:
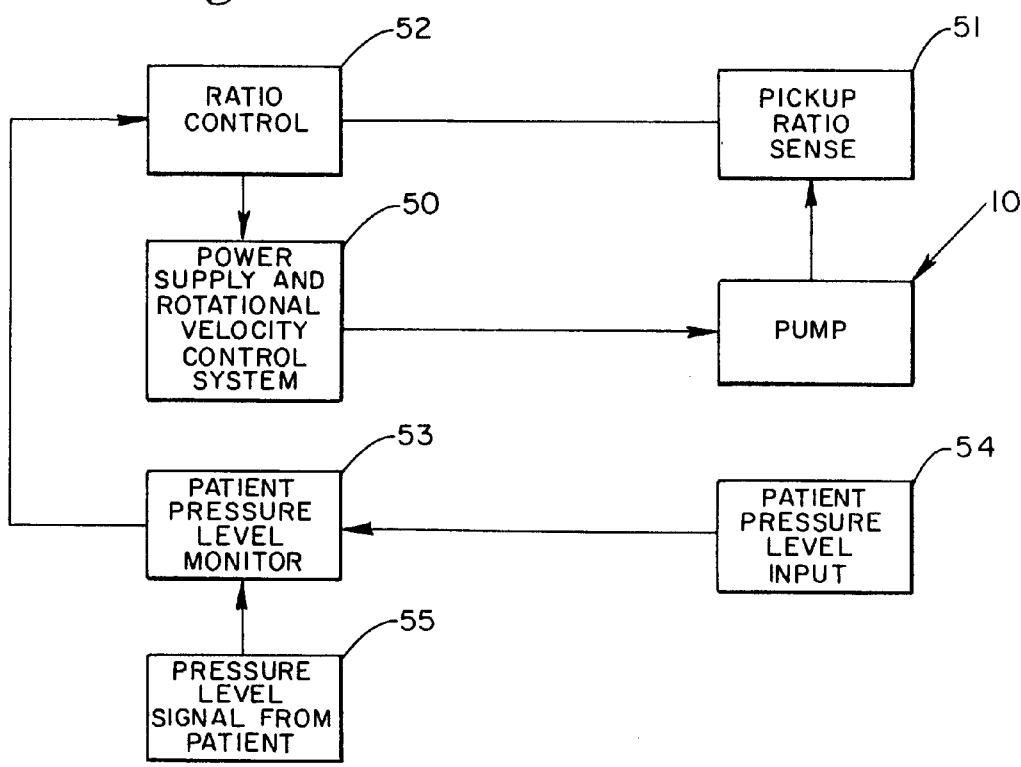
FIG. 5 is a schematic diagram illustrating a typical system in which the device of the present invention may function.

Attention is now directed to FIG. 5 of the drawings wherein the pump 10 is coupled in a system which functions as a ventricular or heart-assist device. Pump 10 is powered by power supply 50 and sensors, including pickup ratio sensor 51 and ratio control 52 are employed. The patient pressure level monitor 53 provides an input to ratio control 52 with the level monitor receiving information including patient pressure level input as at 54 and pressure level signal 55. These systems are known in the art and may be employed effectively in connection with the device of the present invention.

While the term "double conical configuration" has been employed throughout, it will be understood that other surfaces of revolution may be employed, such as those surfaces of revolution generated by a curved line such as parabola, or a straight line so as to form a cone. Thus, the term "cone" is understood to be broadly defined herein.

It will be appreciated, of course, that various modifications may be made in the preferred embodiment illustrated above, and these modifications may be made without actually departing from the spirit and scope of the present invention.

What is claimed is:

1. A pump for transferring fluids and comprising a pumping chamber with an inner periphery, an outer periphery and a central axis, a pair of fluid inlet ports arranged in oppositely disposed relationship on said chamber and coaxially with said pumping chamber, an outlet port means arranged transversely and generally medially of said pair of inlet ports, a rotor disposed within said pumping chamber and having a dual conical configuration converging toward opposed polar regions and having an axis of rotation extending between said polar regions and arranged coaxially with the axis of said pumping chamber during operational rotation of said rotor, magnetic driven means arranged on said rotor at radially spaced locations generally symmetrically along said axis of rotation, electromagnetic drive means coupled to a source of energy and arranged to deliver rotational driving energy to said rotor through said magnetic driven means; said rotor comprising:

(a) a body having a density relative to the fluid being pumped substantially less than that of the fluid being pumped and within a range of between about 0.1 and 0.9;
   (b) said body having an axial length and with the axial length along said axis of rotation defining the axial length of said pumping chamber disposed between said inlet ports; and with the diameter of said rotor body transverse to said axis of rotation defining a medial plane and the axial length and the diameter being selected to provide a clearance between the outer surface of said rotor and the inner surface of said pumping chamber;
   (c) a plurality of radial vanes mounted on the outer peripheral surfaces of said rotor and extending in an axial direction from a plane through the center of said rotor transverse to the axis of rotation thereof, and with the outer peripheral edges of said vanes being spaced from the inner peripheral surface of said housing along an approximately constant dimension and with the cross-sectional area of the inlet ports being substantially equal to that of the outlet ports, thereby providing for hydrodynamic balance of said rotor.

2. The pump of claim 1 wherein said clearance between the inner surface of said pumping chamber and the outer surface of said rotor is adequate to provide a flow channel for blood and is such that the velocity of fluid being pumped remains substantially constant between said inlet ports and outlet ports relative to the surface of said housing.

3. The pump of claim 1 wherein the rate of rotation of said rotor is controllably variable.

4. The pump of claim 1 being particularly characterized in that means are provided for sensing the rotational velocity of said rotor.

5. The pump of claim 1 being particularly characterized in that the driving forces for said rotor are coupled to magnetic driven means disposed symmetrically about the center of mass of the rotor.

6. The pump of claim 1 being particularly characterized in that the fluid flows from inlets adjacent the polar tips of the cones to an outlet adjacent the medial plane.

7. The pump as defined in claim 5 wherein the drive means includes permanent magnets arranged within the rotor along radial points adjacent the outer circumference of the rotor.

8. The pump as defined in claim 1 wherein the drive means includes permanent magnets disposed in a circular array, and wherein the outer perimeter of the magnets forming the array is adjacent the outer circumference of the rotor adjacent the mid-point thereof, and with the structural mass of the rotor being disposed adjacent the rotational axis, thereby reducing the moment of inertia of said rotor.

9. A pump for transferring fluids and comprising a pumping chamber with an inner periphery, an outer periphery and a central axis, inlet port means arranged in polar relationship to said pumping chamber and coaxially with said pumping chamber during operational rotation of said rotor, an outlet port means arranged transversely and generally medially of said pair of inlet ports, a rotor disposed within said pumping chamber and having a dual conical configuration converging toward opposed polar regions and having an axis of rotation extending between said polar regions and arranged coaxially with the axis of said pumping chamber, magnetic driven means arranged on said rotor at radially spaced locations generally symmetrically of said axis of rotation, electromagnetic drive means coupled to a source of energy and arranged to deliver rotational driving energy to said rotor through said magnetic driven means; said rotor comprising:

(a) a body having a relative density of between 10% and 90% of the density of the fluid being pumped;

(b) said body having radial vanes along the ends thereof, with the outer edge configuration of the vanes mounted on said body having an axial length and with the axial length along said axis of rotation defining a substantial portion of the axial length of said pumping chamber between said inlet ports; and with the configuration and diameter of said rotor body transverse to said axis of rotation defining a medial plane and being selected to provide a clearance between the outer surface of said rotor and the inner surface of said pumping chamber and with the magnitude of the clearance between the said inner surface of said pumping chamber and the outer surface of said rotor being generally constant from said inlet ports to said outlet port means; and (c) the arrangement being such that the sole support for the rotor are the hydrodynamic forces created in the fluid being pumped, wherein the casing structure of the pump is free of rotor supporting members and bearings.

* * * * *